United States Patent
Sanchez et al.

(10) Patent No.: US 6,803,775 B2
(45) Date of Patent: Oct. 12, 2004

(54) FUEL QUALITY SENSOR ASSEMBLY AND METHOD OF USE

(75) Inventors: Ramon A Sanchez, Juarez (MX); Santos Burrola, Juarez (MX)

(73) Assignee: Delphi Technologies, Inc., Troy, MI (US)

( * ) Notice: Subject to any disclaimer, the term of this patent is extended or adjusted under 35 U.S.C. 154(b) by 40 days.

(21) Appl. No.: 10/254,347

(22) Filed: Sep. 25, 2002

(65) Prior Publication Data

US 2004/0056670 A1 Mar. 25, 2004

(51) Int. Cl.[7] .................. G01R 27/08; G01R 31/08; G01F 1/58
(52) U.S. Cl. .................. 324/698; 324/724; 324/515; 73/861.15
(58) Field of Search ................. 324/698, 722, 324/515, 695, 664, 693, 691, 724; 123/494, 511; 73/861.15, 53.05

(56) References Cited

U.S. PATENT DOCUMENTS

| | | | |
|---|---|---|---|
| 2,679,027 A | * | 5/1954 | Clark .................. 324/696 |
| 3,320,529 A | * | 5/1967 | Vreeland et al. .......... 324/693 |
| 4,905,655 A | * | 3/1990 | Maekawa .................. 123/494 |
| 4,915,084 A | | 4/1990 | Gonze .................... 123/575 |
| 5,179,926 A | | 1/1993 | Ament .................... 123/494 |
| 5,208,544 A | * | 5/1993 | McBrearty et al. ........ 324/687 |
| 5,255,656 A | | 10/1993 | Rader et al. ............. 123/494 |
| 5,331,287 A | * | 7/1994 | Yamagishi et al. ........ 324/724 |
| 6,318,405 B1 | | 11/2001 | Brandt et al. ........... 137/484.2 |
| 6,325,048 B1 | | 12/2001 | Robinson ................. 123/463 |
| 6,453,733 B1 | | 9/2002 | Malaczynski et al. ...... 123/644 |
| 6,520,166 B1 | | 2/2003 | Karau et al. ............. 73/116 |
| 2002/0011095 A1 | | 1/2002 | Park et al. .............. 73/54.01 |

* cited by examiner

Primary Examiner—Anjan K. Deb
(74) Attorney, Agent, or Firm—Jimmy L. Funke

(57) ABSTRACT

A sensing element (2) for sensing a fluid (50) composition and a method of using the sensing element (2) are provided. The sensing element (2) includes an electrode base (36) having a first electrode (4) and a second electrode (6) disposed on the electrode base (36); the first electrode (4) and a second electrode (6) being electrically isolated one another except through an external circuitry (64); the first electrode (4) and the second electrode (6) defining a gap (42) between one another such that electrical conduction through a fluid (50) within the gap (42) is proportional to the composition of the fluid.

29 Claims, 2 Drawing Sheets

FUEL QUALITY SENSOR ASSEMBLY AND METHOD OF USE

BACKGROUND

Fuel used in internal combustion engines is typically contained in a tank or reservoir as a mixture. Depending on the source of the fuel, it may comprise one or more different fuel components in an unknown ratio. Automobile fuel, for example may be gasoline, including any of its variant blends of aliphatic, olefinic, and/or aromatic hydrocarbons. It may further include various alcohols such as methanol, ethanol, propanol, butanol, pentanol, octanol, and the like. Other components that may be present include octane improvers such as methyl tertiary butyl ether (MTBE) and the like.

Each of these fuel components requires different parameters for optimal combustion. These parameters include specific air to fuel ratios, spark plug timing, injector volume, and the like. When the precise composition of the fuel is unknown, or is ever-changing, accurate determination of the optimal combustion parameters depends on being able to quickly and accurately sense fuel mixture composition and other parameters indicative of optimal end use parameters. One approach to optimal engine operation requires the ability to sense characteristics of the fuel, and adjust the operational conditions of the engine accordingly.

Systems have been designed to sense the characteristics of various blends of fuels, such as gasoline and methanol. U.S. Pat. No. 4,438,749 to Schwippert is directed to an optical sensor that uses the overall refractive index of the fuel as an indication of composition. Aromatic content of the fuel and clouding of the optical sensor elements over time can result in variations of refractive index that lead to inaccuracy in the sensor output.

Microwave fuel composition sensors utilize the fuels overall dielectric constant through microwave attenuation. Besides adding significant cost, these sensors operate at extremely high frequencies (e.g., 1–30 Giga Hertz) and generate amounts of electromagnetic noise that can interfere with other electronic components.

Sensors, which utilize the fuel mixture as a dielectric in a capacitive cell, are also capable of correlating the dielectric constant of a fuel mixture to its composition. These sensors have the benefit of being rugged and can be designed for used in environments in which other sensors would be unacceptable. Unfortunately, the conductivity of various fuel mixtures varies in a non-linear relationship depending on component concentrations. This phenomena is made worse by impurities, especially water. These sensors also need to be made relatively large as compared to other sensors to achieve the level of sensitivity required to sense fuel in an efficient manner. Space and size limitations imposed by design, and the need to minimize void volume in fuel delivery systems, among other factors, have limited the usefulness of capacitive fuel sensors in automotive fuel delivery system applications. A rugged, compact sensor having a sensitivity capable of discriminating between a wide range of fuel blends would be beneficial to optimal combustion of fuel, especially in an internal combustion engine.

SUMMARY

Described herein is a sensing element for measuring a fluid composition comprising: an electrode base having a first electrode and a second electrode disposed thereon; the first electrode and said second electrode being electrically isolated from one another; said first electrode and said second electrode being configured, dimensioned, and positioned to define a gap therebetween such that electrical conduction through the fluid within said gap is proportional to the composition of said fluid.

Also disclosed is a method of sensing a fluid composition comprising: contacting said fluid composition with a sensing element in communication with a circuitry, said sensing element comprising: an electrode base having a first electrode and a second electrode disposed thereon; said first electrode and said second electrode being electrically isolated from one another, except through said circuitry; said first electrode and said second electrode being configured, dimensioned, and positioned to define a gap therebetween such that electrical conduction through a fluid within said gap is proportional to the composition of said fluid; a first electrical connector to provide electrical communication between said first electrode and said circuitry; and a second electrical connector to provide electrical communication between said second electrode and said circuitry; determining said electrical conduction of said fluid; and correlating said electrical conduction to said fluid composition.

Further disclosed herein is a combined fluid pressure regulator and assembly for sensing a fluid composition, comprising: a sensing element disposed within a fluid flow path located within a fluid pressure regulator housing; said sensing element comprising: an electrode base having a first electrode and a second electrode disposed thereon; said first electrode and said second electrode being electrically isolated from one another except through an external circuitry; said electrode base having an inner surface and an outer surface separated by a thickness; said outer surface being continuously disposed around a central axis to form an essentially cylindrical shape; said electrode base defining a flow path parallel to said central axis having a flow path length; said first electrode being a plurality of first electrode teeth disposed on said inner surface depending away from said outer surface towards said central axis; said second electrode being a plurality of second electrode teeth on said inner surface depending away from said outer surface towards said central axis; said first electrode teeth and said second electrode teeth being configured, dimensioned, and positioned in a substantially alternating pattern to define a plurality of gaps therebetween such that electrical conduction through a fluid within said plurality of gaps is proportional to a composition of said fluid; said fluid pressure regulator housing comprising a first fluid conduit and a second fluid conduit which allows said fluid to travel through said fluid flow path located with said fluid pressure regulator housing; a regulator valve mounted therein responsive to a fluid demand and disposed in sealing communication between said first conduit and a bypass conduit; a first electrical connector being channeled through a sealing member disposed in said regulator valve to provide electrical communication between said first electrode and said external circuitry; and a second electrical connector being channeled through a sealing member disposed in said regulator valve to provide electrical communication between said second electrode and said external circuitry.

The above described and other features are exemplified by the following figures and detailed description.

DRAWINGS

Referring now to the figures wherein like elements are numbered alike:

DETAILED DESCRIPTION

Dielectric constant is indicative of a fluid's composition, and can be measured and used either alone or in combination with other measured values to provide information as to the fluid composition. This information can in turn be used to set optimal combustion parameters within an internal combustion engine.

Figure 1:
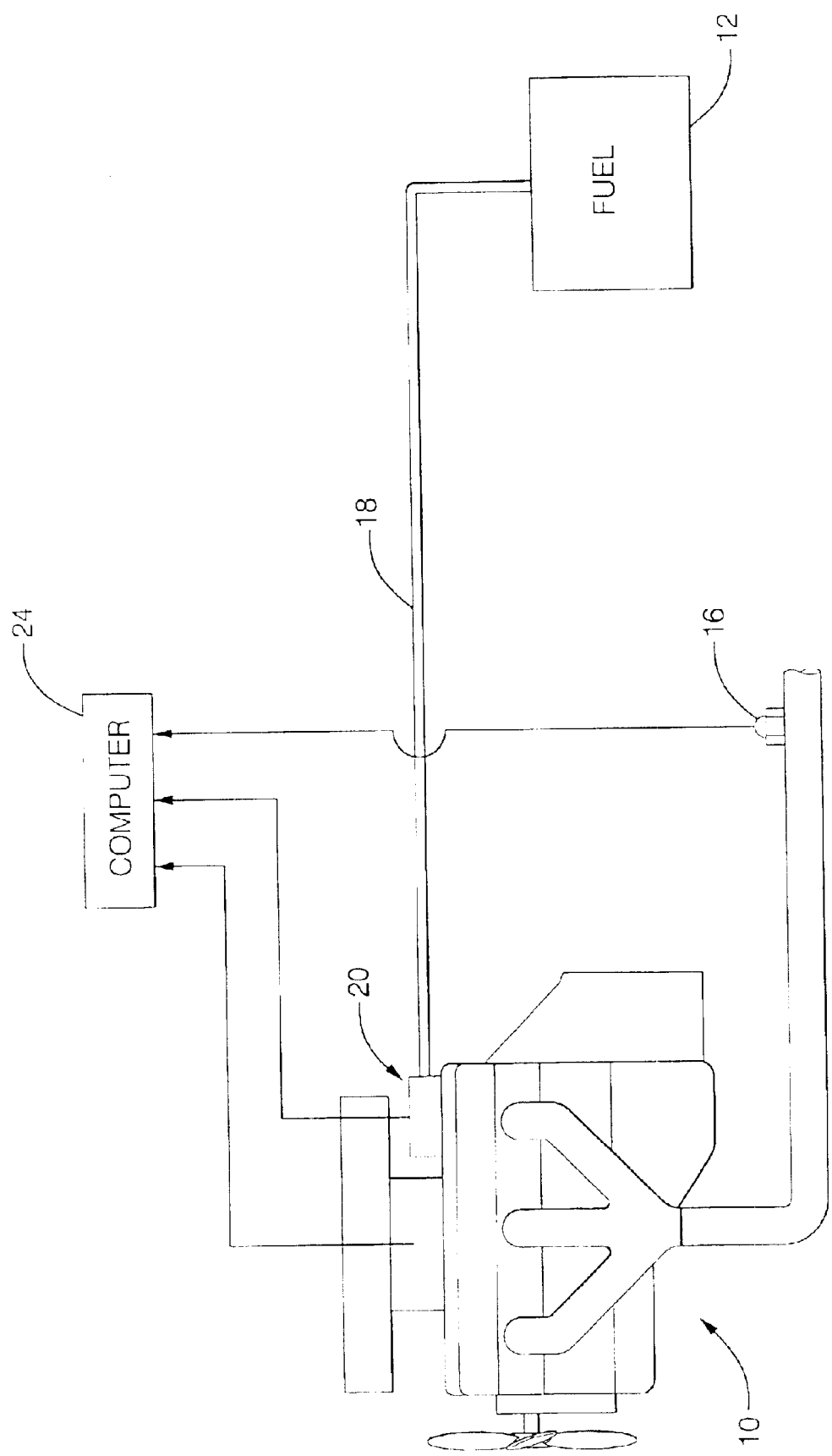
FIG. 1 shows a combustion engine having a fuel composition sensor.

Referring now to FIG. 1, a sensor assembly 20 is incorporated in a fuel delivery system for an internal combustion engine 10. Sensor assembly 20 generates a signal indicative of the conductance between two electrodes (e.g., the dielectric constant) of the fluid (e.g., fuel mixture) about to enter the combustion chamber of engine 10. This signal serves as an input to a circuitry (e.g., a computer) 24 for adjustment of the combustion parameters generated by whatever algorithm, or combinations of various algorithms used in the computer 24 either alone or in combination with other inputs such as exhaust gas composition, engine temperature, ambient temperature, atmospheric pressure, elevation, ambient air composition and the like.

Figure 2:
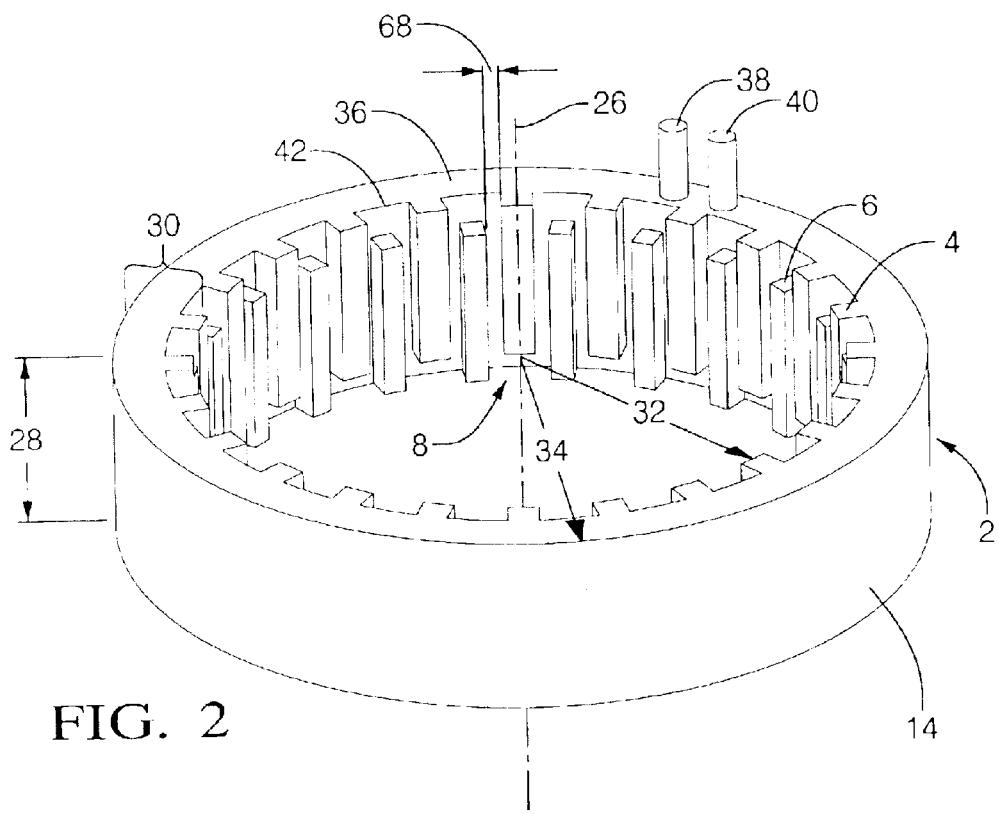
FIG. 2 shows a sensing element described herein.

An embodiment of the sensing element used by the sensor assembly 20 is shown in FIG. 2. The sensing element 2 includes a first electrode depicted as a plurality of first electrode teeth 4 and a second electrode, depicted as a plurality of second electrode teeth 6 disposed on electrode base 36 of sensing element 2. As shown in FIG. 2, first electrode teeth 4 may be formed from the electrode base 36. It is important that the first electrodes 4 and the second electrodes 6 be electrically isolated from each other. As used herein, the term "electrically isolated" is used to indicate a lack of direct electrical contact or conduction, but can include and/or allow for an electrical connection through an external circuitry.

The materials from which the sensing element 2 is constructed depend on the environment in which the sensor will operate. For use in a fuel delivery system, for example, the sensing element 2 may be formed from any material suitable for use with hydrocarbons blends such as, for example gasoline; alcohols, such as, for example, methanol, ethanol, propanol and the like; ethers, such as, for example, MTBE and other organic materials. In addition, the materials must be stable in the presence of contaminants present in the fuel mixture including water, sulfur, and the like. The electrode base 36 may be electrically conductive or nonconductive. In one embodiment, the electrode base 36 is electrically conductive, being constructed from a metal or metal alloy. Examples of suitable materials include steel, stainless steel, iron, nickel, gold, silver, platinum and the like with gold being most preferred. In an alternative embodiment, the electrode base is a nonconductive ceramic having the electrodes disposed thereon using, for example, a metal ink or inlay.

The shape of the electrode base 36 generally defines a three-dimensional solid disposed around a central axis 26. Preferably, the shape is continuously disposed around the central axis to form a hollow three-dimensional solid having a plurality of sides spaced around the central axis 26. The inner surface 8 of electrode base 36 is separated from the outer surface 14 by a thickness 30. By hollow, it is meant a fluid passage is present along and substantially parallel to the central axis 26 within the hollow portion of the electrode base 36. This fluid passage in turn defines a flow path having a fluid passage length 28 corresponding to the height of the sensing element 2.

Preferably, the cross section taken perpendicular to this central axis 26 through the plane of the sensing element 2 defines a hollow polygon. By hollow polygon, it is meant two geometric shapes are coaxially disposed one within the other (e.g., an outer and an inner polygon), such as, for example, concentric hexagons, octagons, circles, ovals, squares and the like.

The inner surface 8 is separated from the central axis 26 by an inner dimension 32. The outer surface is separated from the central axis 26 by an outer dimension 34. The inner dimension 32 and the outer dimension 34 need not be uniform at every point on the sensing element. For example, when the outer surface 14 of the sensing element approximates an oval, the outer dimension 34 will vary depending on the radial position of the point from which this dimension is measured. The same holds true for essentially all geometric shapes with the exception of a cylinder. Also, since the inner surface 8 need not define the same shape, as does the outer surface 14, the thickness 30, which separates the inner, and the outer surfaces need not remain uniform throughout.

Preferably, the two dimensional cross-section of the sensing element defines an outer polygon having an infinite number of sides, (i.e., a circle). Also preferably, the three dimensional shape of the sensing element 2 is essentially cylindrical, and the outer dimension 34 is the outer radius of the cylinder, the inner dimension 32 is the inner radius of the cylinder, and the fluid passage length 28 is the height of the cylinder.

First electrode teeth 4, and second electrode teeth 6 may each have a shape that is essentially rectangular, rounded, pointed, and/or the like, depending on the environmental conditions in which the sensor will operate. Preferably, the outer contours of the electrode teeth each define a rectangular solid having a major axis perpendicular to the central axis 26.

Each one of the second electrode teeth 6 must be disposed in proximity to the first electrode teeth 4, and must remain electrically isolated from the first electrode teeth 4, except as connected through external circuitry. Preferably, each one of the second electrode teeth 6 are uniformly disposed in a substantially alternating pattern between at least one each of the first electrode teeth 4 defining an essentially uniform gap 42 there between (e.g., a first electrode, then a second electrode, then a first electrode) each being configured, dimensioned, and positioned to define the gap 42 there between such that electrical conduction through a fluid within the gap is proportional to the compositional makeup of the fluid.

The gap width 68 is defined herein as the average distance between a side of the first electrode and a corresponding side of the second electrode that faces the side of the first electrode. The actual value of the gap width 68 depends on the characteristics of the fluid, and the operational conditions in which the sensing electrode is used. When used in a fuel delivery system, for example, this gap is on average about 0.01 millimeters (mm) to about 10 mms wide. Preferably within this range, the gap is greater than or equal to about 0.1 more preferably greater than or equal to about 0.5 mms between each of the two electrodes. Also within this range, the gap is less than or equal to about 2, more preferably less than or equal to about 1 mm between each of the two electrodes.

The structures (e.g., teeth) that form the first electrode teeth 4 are all preferably in electrical contact with one another to form a single first electrode. Also, the structures that form the second electrode teeth 6 are all preferably in electrical contact with one another to form a single second electrode. First and second electrical connectors 38 and 40 provide electrical conductivity between the electrodes and external circuitry. Both of which are in electrical contact with their respective electrodes 4 and 6, but are electrically isolated from each other. The multiple teeth or other such structures serve to increase the available surface area available for sensing given the total size of the sensing element. This is important because the overall sensitivity of the sensing element increases as the available surface area increases.

The value of the outer dimension 34, the inner dimension 32, and the fluid passage length 28 depend on the characteristics required of the sensor element 2. Each of these two electrodes also has an associated total surface area. By defining the total surface area of the electrodes as being the underlying geometric surface area (e.g., for a rectangle, base multiplied by height), the total surface area of the first electrode, when the sensor is used, for example, in a fuel delivery system, is greater than or equal to about 50 square millimeters ($mm^2$) Preferably within this range, the total surface area of the first electrode is greater than or equal to about 90, more preferably greater than or equal to about 300 $mm^2$ as represented by the underlying geometric area.

Also, by defining the total surface area of the first electrode as being equal to unity (i.e., equal to one), the proportion of the total surface area of the first electrode to the total surface area of the second electrode determined in the same way is a ratio of about 1 to 0.01, to a ratio of about 1 to 100. Preferably within this range, the proportion of total surface areas of the first electrode to the total surface area of the second electrode is a ratio of greater than or equal to about 1 to 0.1, more preferably greater than or equal to about 1 to 0.5. Also within this range, the proportion of total surface areas of the first electrode to the total surface area of the second electrode is a ratio of less than or equal to about 1 to 10, more preferably less than or equal to about 1 to 2, with a ratio of 1:1 being most preferred.

The sensing element is preferably located within a housing to form a sensing assembly 20. The sensing element 2 is disposed within the housing and arranged such that the fluid of interest is able to occupy the gaps 42 between the electrodes and thus be in contact with the sensing element. Preferably, the housing is closed except for a fluid inlet conduit and a fluid outlet conduit. The housing provides a conduit or flow path between the inlet an outlet conduits, and in communication with the sensing element. Preferably, the fluid is able to enter the housing, contact the sensing element along the fluid passage length 28, and then exit the housing.

When used to determine the composition of fuel for an internal combustion engine, for example, the sensing assembly is preferably located in close proximity to the point at which the fuel is combusted and also preferably has a total volume that does not interfere with optimal combustion of the fuel.

To prevent extraneous effects between the housing and the sensing element, the shape of the housing is preferably complementary to the shape of the outer surface of the sensing element. As used herein the term complementary is defined as the two being essentially the same. For example, when the outer surface of the sensing element is essentially cylindrical, the housing is thus preferably essentially cylindrical and the housing also has an inner diameter in excess of the outer diameter of the sensing element to allow fuel to freely flow within the housing.

Figure 3:
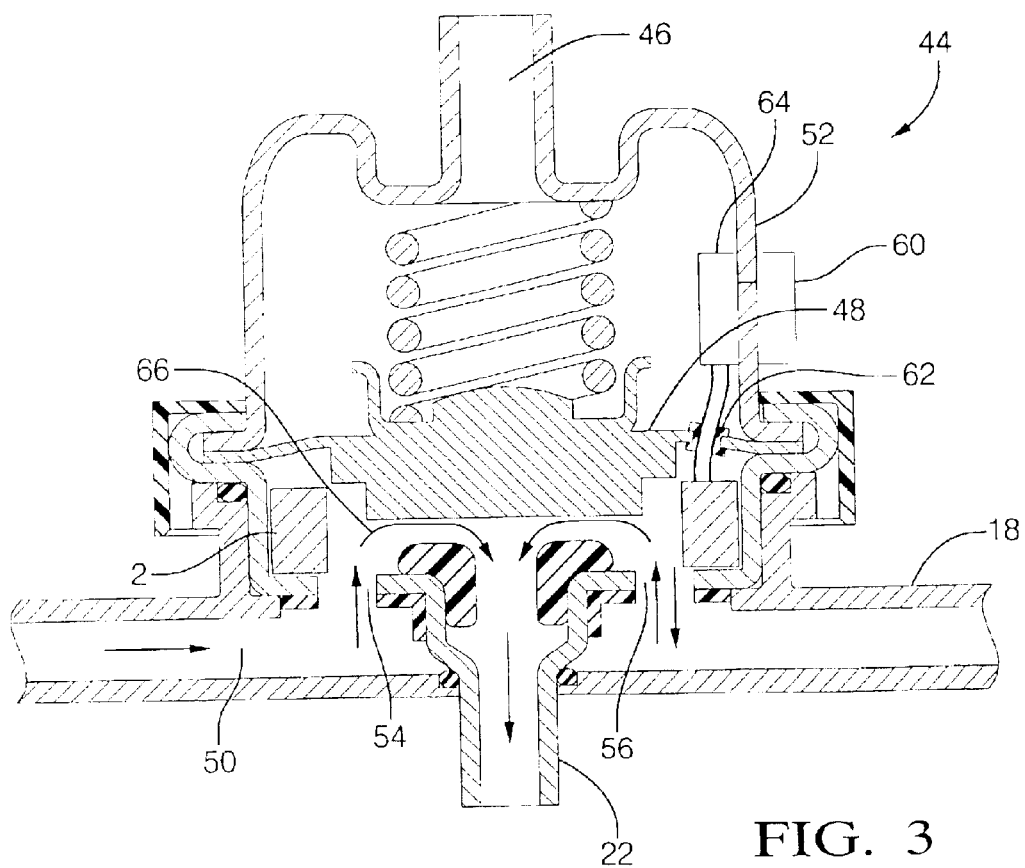
FIG. 3 shows the sensing element of FIG. 2 disposed in a fuel pressure regulator housing.

In the embodiment shown in FIG. 3, the sensing element 2 is disposed within a fuel pressure regulator 44. Within the fuel pressure regulator-housing 52 is a regulator valve 48 disposed in sealing communication between a fluid rail conduit 18, and a bypass conduit 22. Preferably, the regulator valve 48 is responsive to fluid demand via pneumatic communication with an air intake manifold through manifold conduit 46. In this arrangement, the sensor element 2 is concentrically disposed within, and bounded by the fuel pressure regulator housing 52 and by the regulator valve 48. A fluid conduit or flow path 66 between the fuel rail inlet 54 and the fuel rail outlet 56 is provided by the regulator housing 52 such that the sensing element 2 is located within this flow path 66.

Electrical connection between the sensing element 2 and an external electronic system is preferably provided by directing the electrical connectors 38 and 40 through a sealing member 62 located within the regulator valve assembly 44, and preferably to an external electrical connector 60. Also, a portion of and/or all of the necessary electronics may be located as on electronics package 64 within a portion of the housing 52, depending on space limitations and design needs.

The sensor is in communication with, and preferably electrically connected to an electronic circuitry capable of providing information as to the composition of the fluid the sensor comes in contact with. The electronic circuitry may include a computer or computers capable of using the information derived from the sensor to adjust the combustion parameters of the engine to an optimal value for the fuel mixture flowing through sensor. For this purpose, the computer or computers can include a standard read only memory (ROM) containing a multiple dimensioned lookup table containing compensation factors to be repeatedly looked up with a combination of capacitance and other factors including ambient and engine temperature, exhaust gas composition, ambient air analysis and the like. These compensation factors can be used directly, or can be associated with additional inputs and lookup tables.

While preferred embodiments have been shown and described, various modifications and substitutions may be made thereto without departing from the spirit and scope of the invention. Accordingly, it is to be understood that the apparatus and method have been described by way of illustration only, and such illustrations and embodiments as have been disclosed herein are not to be construed as limiting to the claims.

We claim:
1. A sensing element for measuring a fluid composition comprising:
an electrode base being disposed about an axis, said electrode base having an inner surface defining an aperture extending through the electrode base for allowing a fluid to flow therethrough; and
a first electrode and a second electrode coupled to said electrode base and electrically isolated from one another, said first electrode having a first plurality of electrode teeth extending radially inwardly from said inner surface of the electrode base into said aperture, and said second electrode having a second plurality of electrode teeth extending radially inwardly from said inner surface into said aperture, said first plurality of electrode teeth being electrically connected together, and said second plurality of electrode teeth being electrically connected together, wherein said second plurality of electrode teeth are arranged in a substan- tially alternating pattern between said first plurality of electrode teeth to form a plurality of gaps between each of said first plurality of electrode teeth and said second plurality of electrode teeth, wherein electrical conduction through the fluid between said plurality of gaps is indicative of the composition of said fluid.

2. The sensing element of claim 1, wherein said electrode base and said first electrode are in electrical communication.

3. The sensing element of claim 1, wherein said electrode base has both said inner surface and an outer surface disposed around said axis;
   said inner surface being separated from said outer surface by a thickness; and
   said electrode base defining a flow path parallel to said axis, and
   said flow path having a flow path length.

4. The sensing element of claim 3, wherein said outer surface is continuous about said axis.

5. The sensing element of claim 3, wherein the total surface area of said first electrode is greater than or equal to about 50 square millimeters.

6. The sensing element of claim 3, wherein a ratio of the total surface area of said first electrode to the total surface area of said second electrode is about 1:0.01 to about 1:100.

7. The sensing element of claim 3, wherein the total surface area of said first electrode is about equal to the total surface area of said second electrode.

8. The sensing element of claim 1, wherein each of said gaps is on average about 0.01 to about 10 millimeters wide.

9. A sensing assembly comprising the sensing element of claim 1, wherein said sensing element is disposed within a housing within a fluid passage conduit formed between a first fluid conduit and a second fluid conduit which allows said fluid to travel through said housing;
   a first electrical connector being channeled through said housing to provide electrical communication between said first electrode and a circuitry; and
   a second electrical connector being channeled through said housing to provide electrical communication between said second electrode and said circuitry.

10. The sensing assembly of claim 9, wherein the housing has a shape complementary to the outer surface of the sensing element.

11. The sensing assembly of claim 9, wherein said housing is a fuel pressure regulator including a regulator valve mounted therein responsive to a fuel demand and disposed in sealing communication between said first conduit and a bypass conduit.

12. The sensing assembly of claim 11, wherein said first electrical connector and said second electrical connector are channeled through a sealing member disposed in said regulator valve.

13. The sensing element of claim 1, wherein said electrode base comprises a substantially ring-shaped electrode base.

14. The sensing element of claim 1, wherein said fluid comprises a fuel for an internal combustion engine.

15. A method of sensing a fluid composition comprising:
   contacting said fluid composition with a sensing element in communication with a circuitry, said sensing element comprising:
      an electrode base being disposed about an axis, said electrode base having an inner surface defining an aperture extending through the electrode base for allowing a fluid to flow therethrough, and a first electrode and a second electrode coupled to said electrode base and electrically isolated from one another, said first electrode having a first plurality of electrode teeth extending radially inwardly from said inner surface of the electrode base into said aperture, and said second electrode having a second plurality of electrode teeth extending radially inwardly from said inner surface into said aperture, said first plurality of electrode teeth being electrically connected together, and said second plurality of electrode teeth being electrically connected together, wherein said second plurality of electrode teeth are arranged in a substantially alternating pattern between said first plurality of electrode teeth to form a plurality of gaps between each of said first plurality of electrode teeth and said second plurality of electrode teeth, wherein electrical conduction through the fluid between said plurality of gaps is indicative of the composition of said fluid, and a first electrical connector to provide electrical communication between said first electrode and said circuitry; and a second electrical connector to provide electrical communication between said second electrode and said circuitry;
   determining said electrical conduction of said fluid; and
   correlating said electrical conduction to said fluid composition.

16. The method of claim 15, wherein said electrode base and said first electrode are in electrical communication.

17. The method of claim 15, wherein said electrode base has both said inner surface and an outer surface disposed around said axis;
   said inner surface being separated from said outer surface by a thickness;
   said electrode base defining a flow path parallel to said axis; and
   said flow path having a flow path length.

18. The method of claim 17, wherein the total surface area of said first electrode is greater than or equal to about 50 square millimeters.

19. The method of claim 17, wherein a ratio of the total surface area of said first electrode to the total surface area of said second electrode is about 1:0.01 to about 1:100.

20. The method of claim 17, wherein the total surface area of said first electrode is about equal to the total surface area of said second electrode.

21. The method of claim 15, wherein said outer surface is continuous about said axis.

22. The method of claim 15, wherein each of said gaps is on average about 0.01 to about 10 millimeters wide.

23. The method of claim 15, wherein said sensing element is disposed within a housing within a fluid passage conduit formed between a first fluid conduit and a second fluid conduit which allows said fluid to travel through said housing;
   a first electrical connector being channeled through said housing to provide electrical communication between said first electrode and a circuitry; and
   a second electrical connector being channeled through said housing to provide electrical communication between said second electrode and said circuitry.

24. The method of claim 23, wherein the housing has a shape complementary to the outer surface of the sensing element.

25. The method of claim 23, wherein said housing is a fuel pressure regulator including a regulator valve mounted therein responsive to a fuel demand and disposed in sealing communication between said first conduit and a bypass conduit.

26. The method of claim 25, wherein said first electrical connector and said second electrical connector are channeled through a sealing member disposed in said regulator valve.

27. A combined fluid pressure regulator and assembly for sensing a fluid composition, comprising:

a sensing element disposed within a fluid flow path located within a fluid pressure regulator housing;

said sensing element comprising:

an electrode base having a first electrode and a second electrode disposed thereon;

said first electrode and said second electrode being electrically isolated from one another except through an external circuitry;

said electrode base having an inner surface and an outer surface separated by a thickness;

said outer surface being continuously disposed around a central axis to form an essentially cylindrical shape;

said electrode base defining a flow path parallel to said central axis having a flow path length;

said first electrode being a plurality of first electrode teeth disposed on said inner surface depending away from said outer surface towards said central axis;

said second electrode being a plurality of second electrode teeth on said inner surface depending away from said outer surface towards said central axis;

said first electrode teeth and said second electrode teeth being configured, dimensioned, and positioned in a substantially alternating pattern to define a plurality of gaps therebetween such that electrical conduction through a fluid within said plurality of gaps is proportional to a composition of said fluid;

said fluid pressure regulator housing comprising a first fluid conduit and a second fluid conduit which allows said fluid to travel through said fluid flow path located with said fluid pressure regulator housing;

a regulator valve mounted therein responsive to a fluid demand and disposed in sealing communication between said first conduit and a bypass conduit;

a first electrical connector being channeled through a sealing member disposed in said regulator valve to provide electrical communication between said first electrode and said external circuitry; and a second electrical connector being channeled through a sealing member disposed in said regulator valve to provide electrical communication between said second electrode and said external circuitry.

28. A sensing element for measuring a fluid composition comprising:

a substantially ring-shaped electrode base being disposed about an axis, said electrode base having an inner surface defining an aperture extending through the electrode base for allowing a fluid to flow therethrough; and a first electrode and a second electrode coupled to said electrode base and electrically isolated from one another, said first electrode having a first plurality of electrode teeth extending radially inwardly, from said inner surface of the electrode base into said aperture, and said second electrode having a second plurality of electrode teeth extending radially inwardly, from said inner surface into said aperture, wherein said second plurality of electrode teeth are arranged in a substantially alternating pattern between said first plurality of electrode teeth to form a plurality of gaps between each of said first plurality of electrode teeth and said second plurality of electrode teeth, wherein electrical conduction through the fluid between said plurality of gaps is indicative of the composition of said fluid.

29. The sensing element of claim 28, wherein said fluid comprises a fuel for an internal combustion engine.

* * * * *